(12) United States Patent
Mason

(10) Patent No.: US 6,743,631 B1
(45) Date of Patent: Jun. 1, 2004

(54) USE OF HUMAN SERUM RESISTANT VECTOR PARTICLES AND CELL LINES FOR HUMAN GENE THERAPY

(75) Inventor: James M. Mason, Bethpage, NY (US)

(73) Assignee: North Shore University Hospital Research Corporation, Manhasset, NY (US)

( * ) Notice: Subject to any disclaimer, the term of this patent is extended or adjusted under 35 U.S.C. 154(b) by 0 days.

(21) Appl. No.: 09/040,103

(22) Filed: Mar. 17, 1998

(51) Int. Cl.$^7$ .................. C12N 15/867; C12N 15/63; C12N 5/10; C12N 7/01
(52) U.S. Cl. ............. 435/455; 435/325; 435/456; 435/457; 435/320.1
(58) Field of Search ............................ 435/325, 455, 435/456, 457, 320.1, 5, 6, 352, 373; 424/93.1, 93.2

(56) References Cited

U.S. PATENT DOCUMENTS

| | | | |
|---|---|---|---|
| 4,405,712 A | 9/1983 | Vande Woude et al. | 435/5 |
| 5,562,904 A | 10/1996 | Rother et al. | 424/145.1 |
| 5,576,201 A | 11/1996 | Mason et al. | 435/456 |
| 5,580,766 A | 12/1996 | Mason et al. | 435/456 |
| 5,643,770 A | 7/1997 | Mason et al. | 435/456 |
| 5,871,997 A * | 2/1999 | Rother et al. | 435/235.1 |
| 6,329,199 B1 * | 12/2001 | Pensiero et al. | 435/320.1 |

FOREIGN PATENT DOCUMENTS

| | | |
|---|---|---|
| EP | 0178220 | 4/1986 |
| WO | WO89/07150 | 8/1989 |
| WO | WO92/07943 | 5/1992 |

OTHER PUBLICATIONS

Marshall, Science, 2003, vol. 299, No. 5605, p. 320.*
Mountain, TIBTECH, 2000, vol. 18, pp. 119–128.*
Kmiec, American Scientist, 1999, vol. 87, pp. 240–247.*
Anderson, Nature, 1998, vol. 392, pp. 25–30.*
Lie et al., J. Virol., vol. 68, No. 12, pp. 7840–7849, Dec. 1994.*
Chong & Vile, "Replication–Competent Retrovirus Produced by a 'Split–function' Third Generation Amphotropic Packaging Cell Line", Gene Ther., 3:624–629, 1996.
Cone & Mulligan, "High–efficiency Gene Transfer into Mammalian Cells: Generation of Helper–free Recombinant RetroVirus with Broad Mammalian Host Range", Proc. Natl'l. Acad. Sci. USA, 81:6349–6353, 1984.
Cosset, et al., "High–titer Packaging Cells Producing Recombinant Retroviruses Resistant to Human Serum", J. Virol., 69:7430–7436, 1995.
Crystal, "Transfer of Genes to Humans: Early Lessons and Obstracles to Success", Science, 270:404–410, 1995.
Culver, et al., "In Vivo Gene Transfer with Retroviral Vector–producer Cells for Treatment of Experimental Brain Tumors", Science, 256:1550–1552, 1992.
Eglitis, "Positive Selectable Markers for Use with Mammalian Cells in Culture", Hum. Gene Ther., 2:195–201, 1991.
Eglitis & Anderson, "Retroviral Vectors for Introduction of Genes into Mammalian Cells", Biotechniques, 6:608–614, 1988.
Galili, et al., "Evolutionary Relationship Between the Natural Anti–gal Antibody and the Galα–3gal Epitope in Primates", Proc. Natl'l. Acad. Sci. USA, 84:1369–1373, 1987.
Gilboa, et al., "Transfer and Expression of Cloned Genes Using Retroviral Vectors", Biotechniques, 4:504–512, 1986.
Girod, et al., "Homologous and Nonhomologous Retroviral Recombinations Are Both Involved in the Transfer by Infectious Particles of Defective Avian Leukosis Virus–derived Transcomplementing Genomes", J. Virol., 70:5651–5657, 1996.
Anderson et al., "Endogenous Origin of Defective Retroviruslike Particles from a Recombinant Chinese Hamster Ovary Cell Line," Virology, vol. 181, pp. 305–311 (1991).

* cited by examiner

*Primary Examiner*—David Guzo
(74) *Attorney, Agent, or Firm*—Kenyon & Kenyon

(57) ABSTRACT

The present invention relates to the use of non–primate mammalian cell lines having substantially no endogenous retroviral sequences as producer and packaging lines for preparation of human serum-resistant retroviral vector particles with improved safety for use in gene therapy applications. In a preferred embodiment, the cell line used in the present invention is the α-galactosyl (αGal)-positive cell ferret brain cell line designated as Mpf or a cell line having those identifying characteristics of the Mpf cell line suitable for the practice of the invention.

27 Claims, 3 Drawing Sheets

USE OF HUMAN SERUM RESISTANT VECTOR PARTICLES AND CELL LINES FOR HUMAN GENE THERAPY

FIELD OF THE INVENTION

The present invention relates to the use of non-primate mammalian cell lines having substantially no endogenous retroviral sequences as producer and packaging lines for preparation of human serum-resistant retroviral vector particles. These cell lines have improved safety for use in gene therapy applications and can produce high titers of RVP. In a preferred embodiment, the cell line used in the present invention is the α-galactosyl (αGal)-positive, ferret brain cell line designated as Mpf or a cell line having those identifying characteristics of the Mpf cell line suitable for the practice of the invention.

BACKGROUND OF THE INVENTION

Retroviral vector particles (RVP) are functional retrovirus particles engineered to carry heterologous genes. Since RVP are capable of integrating into host mammalian cells as proviral DNA and expressing the heterologous (or foreign) gene, they have found use as therapeutic delivery agents in gene therapy. RVP have several advantages for gene therapy including the ability to efficiently transduce target cells, including human target cells, and integrate into the genomes of those cells at a frequency higher than most other systems. Other advantages include stable expression of the transduced genes, the capacity to transfer large genes, the lack of cellular cytotoxicity and the capacity to transduce mammalian cells from a wide variety of species and tissues.

To produce RVP, a gene of interest is inserted into a retrovirus vector. This vector is introduced into a retroviral packaging cell line to generate a retroviral producer cell line which in turn yields the RVP. Packaging cell lines express retroviral env and gag/pol genes, whereas producer cell lines are essentially packaging cell lines which additionally contain a retrovirus vector. Though not preferred, cell lines which contain only the retroviral vector are useful in some instances since they can be infected with a helper retrovirus. The RVP from such producer lines are, however contaminated with replication competent retrovirus (RCR). Collectively, the retrovirus vector, packaging and producer cell lines and RVP are referred to as a retroviral transduction system.

RVP produced in murine and many other species are not suitable for in vivo gene therapy or ex vivo gene therapy done in the presence of human body fluids (e.g., human serum) because these RVP are lysed in the presence of human serum. The cause of RVP virolysis has been actively investigated and appears to be mediated by the human complement system. For a review of the human complement system and various inhibitors thereof see U.S. Pat. Nos. 5,562,904 and 5,643,770. Some work has demonstrated that the presence of specific viral envelope proteins in the RVP is largely responsible for virolysis, while other work has suggested that the presence of the αGal sugar moieties are the sole or major factor responsible. Still other studies point to multiple factors including unknown packaging cell-specific factors. Based on the demonstration that anti-αGal antibodies in human serum inactivate retroviruses produced from animal cells via a complement-mediated pathway and related experiments (Rother et al. (1995) J. Exp. Med. 182:1345–1355; Takeuchi et al. (1996) Nature 379:85–88), Takeuchi and co-workers have suggested that viral vectors, including retroviral vectors, for human in vivo gene therapy should be prepared from αGal-negative cells (Takeuchi et al. (1997) J. Virol. 71:6174–6178).

Some human cell lines bearing retroviral envelope proteins have been identified which generate serum-resistant RVP; however, this is not a global feature of all human cell lines. In fact, no human cell line has been identified which universally generates serum resistant RVP for the different types of envelope proteins incorporated in the RVP. For example, the human cell line HT1080-Ampho is only 26% resistant to human serum.

While RVP can be made resistant to inactivation by human serum when produced in certain human and Old World primate cell lines, use of these cell lines raises safety related concerns. Human and primate cell lines contain large amounts of endogenous retroviral sequence. In some instances, endogenous retroviral sequences are expressed at the RNA level and in other instances cells shed viral particles or infectious endogenous viruses. It has been reported that up to 1% of RVP can carry inadvertently packaged endogenous retroviral sequences of producer cell origin which can then be effectively transduced into target cells. Replication-defective RVP, bearing only gag-pol or env sequences, have been identified in RVP supernatents and these have been associated with the formation of recombinant, infectious RVP in conjunction with endogenous sequences. Moreover, the demonstration that co-packaged RNA from different viral or endogenous sequences can interact and generate hybrid viruses makes the identification of non-primate cell lines capable of generating high titer, human serum-resistant RVP of significant importance. Use of non-primate cell lines which harbor fewer-endogenous retroviral sequences than conventional packaging cell lines would be an important safety advance in packaging and producer cell line development.

A variety of diseases may be treated by therapeutic approaches that involve stably introducing a gene into a cell such that the gene may be transcribed and the gene product may be produced in the cell. Diseases amenable to treatment by this approach include inherited diseases, particularly those diseases that are caused by a single gene defect. Many other types of diseases, including acquired diseases, may also be amenable to gene therapy. Examples of such acquired diseases include many forms of cancer, lung disease, liver disease, blood cell disorders and vascular disorders. See Anderson (1992) Science 256:808–813; Miller (1992) Nature 357:455–460; and Mulligan (1993) Science 260:926–932.

Delivery of the gene or genetic material into the cell is the first step in gene therapy treatment of disease. A variety of methods have been used experimentally to deliver genetic material into cells. Most research has focused on the use of retroviral and adenoviral vectors for gene delivery. Crystal (1995) Science 270:404–410. As discussed above, RVP are particularly attractive because they have the ability to stably integrate transferred gene sequences into the chromosomal DNA of the target cell and are very efficient in stably transducing a high percentage of target cells.

Most gene therapy protocols involve treating target cells from the patient ex vivo and then reintroducing the cells into the patient. Patients suffering from several inherited diseases that are each caused by a single gene defect have already received gene therapy treatments. Such treatments generally involve the transduction of the patient's cells in vitro using RVP designed to direct the expression of therapeutic molecules, followed by reintroduction of the transduced cells into the patient.

For many diseases, however, it will be desired or necessary to introduce the gene into the target cell in situ, because the target cells cannot be removed from and returned to the body. For example, treatment of ischemic tissue can be done in situ via catheter delivery or direct injection of the gene therapy vector. In other cases, cells that are removed from the patient must be maintained in the presence of body fluids until returned to the body. Stem cells, particularly hematopoietic stem cells, are an especially important type of target cell for gene therapy of inheritable and acquired blood disorders. Such cells are intrinsically unstable in vitro, and tend to differentiate into cells that are less attractive targets for gene therapy, especially when they have been washed free of the fluids that surround them in vivo and transferred into body fluid-free tissue culture media or the like. For example, to transduce stem cells as quickly as possible, ex vivo treatment of such cells with RVP is best carried out in the cells natural milieu, i.e., in cells that have not been washed or otherwise removed from the body fluids in which they are obtained, e.g., hematopoietic stem cells in bone marrow aspirates.

SUMMARY OF THE INVENTION

The present invention is directed to a method for preparing a stable, retroviral packaging cell line for generation of human serum-resistant retroviral vector particles (RVP) which comprises introducing one or more packaging vectors into a non-primate mammalian cell line and recovering that cell line. The cell line of the invention exhibits substantially no hybridization to a Moloney-MLV retrovirus probe under stringent washing conditions and is capable of producing human-serum-resistant RVP. The packaging vectors of the invention, either singly or collectively, express a cellular targeting protein and retroviral gag and pol genes in amounts sufficient to package the RVP. In one embodiment the cell line is the Mpf cell line designated by ATCC accession number 1656CRL. The cellular targeting protein expressed by the packaging vectors of the invention is an amphotropic retroviral env protein, a xenotropic retroviral env protein, a polytropic retroviral env protein, a JSRV env protein, vesicular stomatitis virus G protein or transferrin. The invention also includes the packaging cell lines produced by this method.

The invention further provides a method for preparing stable, retroviral producer cells capable of producing human serum-resistant RVP which comprises introducing a retrovirus vector into the packaging cell line of the invention and recovering the producer cells. The retrovirus vector introduced into the packaging cell line is capable of being packaged into an RVP and comprises a heterologous gene capable of expression in a human. The invention also includes the producer cells produced by this method and RVP prepared from these producer cells.

Another aspect of the invention relates to a method of preparing human serum-resistant RVP which comprises introducing a retrovirus vector into the packaging cell line of the invention, culturing the cell line for a time and under conditions sufficient to produce the RVP and recovering the RVP. This method produces RVP having a supernatant titer on mink cell line Mv-1-Lu of at least about $10^4$ to about $10^8$ colony forming units per milliliter. The invention also includes the RVP produced by this method.

In another method, human serum-resistant RVP are prepared by a method which comprises culturing the producer cells for a time and under conditions sufficient to produce RVP and recovering the RVP. The invention also includes the RVP produced by this method.

Another aspect of the invention relates to a method for transducing a cell with a retroviral vector in the presence of a body fluid which comprises administering the RVP of the invention to the cell to be transduced. The RVP can be administered to the cell er vivo or in vivo.

Yet another aspect of the invention provides a method of gene therapy which comprises delivering a therapeutic molecule encoded on a retrovirus vector to a human cell via an RVP of the invention. Preferably, the therapeutic molecule is a hormone, a growth factor, an enzyme, a lymphokine, a cytokine, a receptor, an angiogenic factor, or an anti-angiogenesis factor. The RVP can be administered to the human cell ex vivo or in vivo.

Still another aspect of the invention is directed to a method for transferring a heterologous gene into a human cell which comprises contacting the human cell with producer cells of the invention under conditions such that the producer cells release RVP containing a retrovirus vector encoding the heterologous gene and thereby introduce that gene into the human cell. The producer cells can be implanted in a human, including in the human brain.

The invention also provides pharmaceutical compositions comprising the RVP of the invention with a pharmaceutically acceptable carrier.

DETAILED DESCRIPTION OF THE INVENTION

Figure 1:
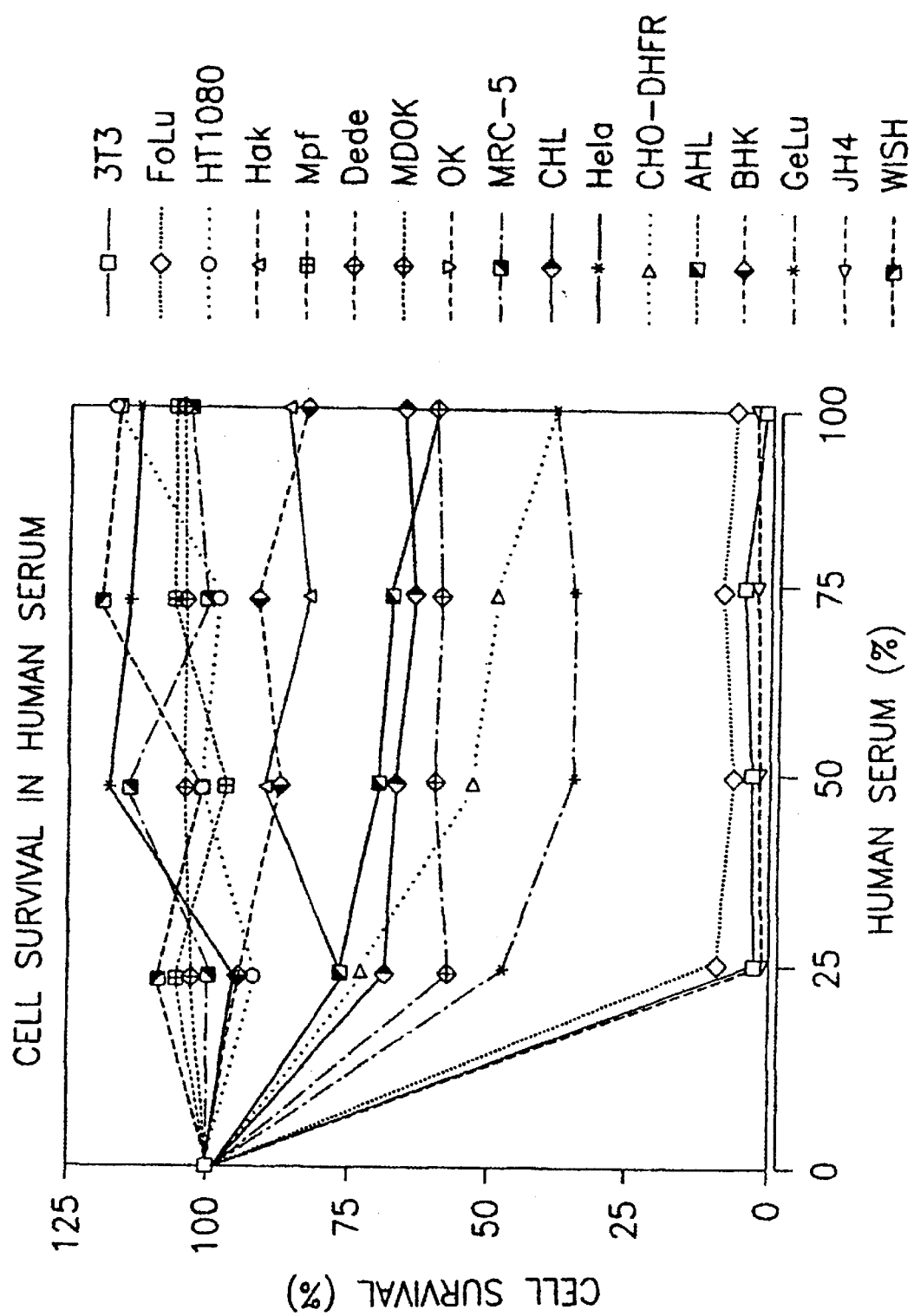
FIG. 1 is a graphic illustration of the percentage cell survival in the presence of various amounts of fresh human serum for seventeen cell lines. the cell lines fall into three classes: fully resistant, partially resistant and sensitive to human serum.
Figure 2:
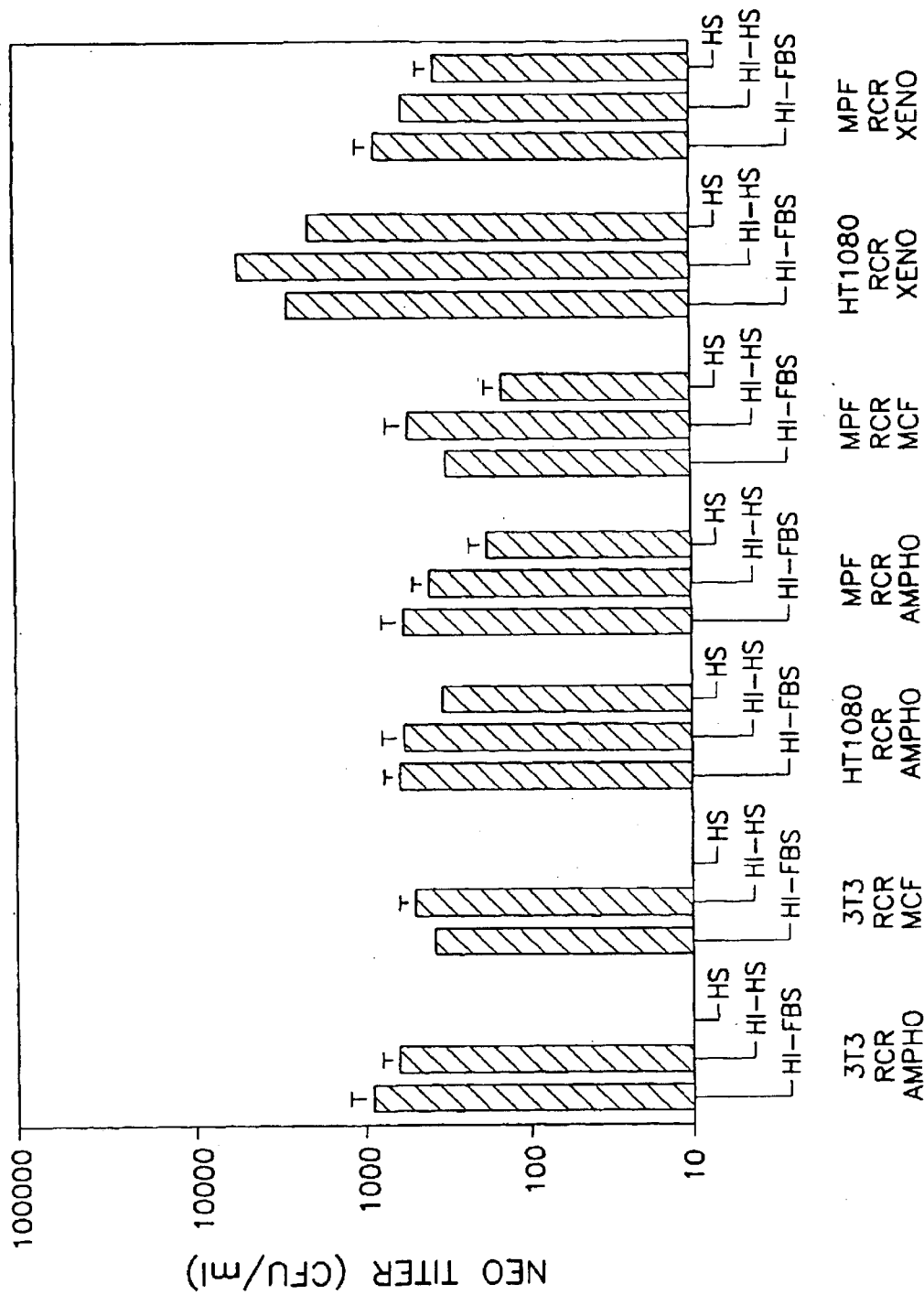
FIG. 2 is a bar graph depicting the titer of neomycin resistant cells (CFU/mL) after incubating RVP with heat-inactivated fetal bovine serum (HI-FBS), heat-inactivated human serum (HI-HS) or fresh human serum (HS) and titering on NIH3T3 cells (FIG. 2A, top panel) or on Mv-1-Lu cells (FIG. 2B, bottom panel). The producer cell line of the RVP is indicated on the first line below each set of three bars, the presence of replication competent retrovirus (RCR) on the second line and the nature of the helper virus on the third line.
Figure 3:
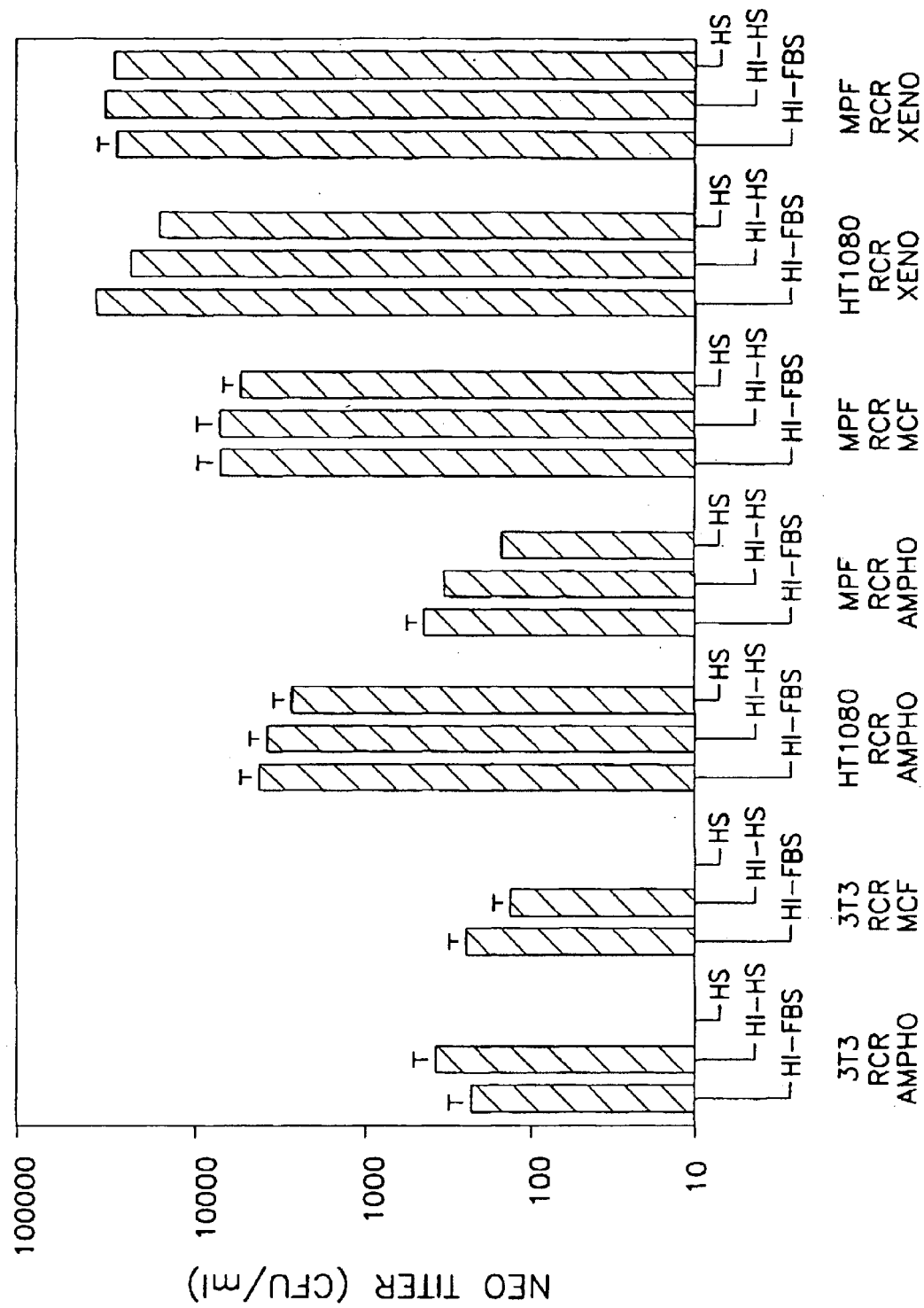

The general techniques used for the subject invention, including constructing packaging vectors and retrovirus vectors used in targeting cells, transforming cells, growing cells in culture, delivering heterologous or foreign genes in vivo or ex vivo for gene therapy, and the like are known in the art and laboratory manuals or other literature references are available describing these techniques.

Unless otherwise indicated, the present invention employs known techniques of gene therapy, molecular biology, cell culture and recombinant DNA which are within the skill of the art. Examples of useful laboratory manuals include Sambrook et al. (1989) *Molecular Cloning: A Laboratory Manual,* 2nd Ed., Cold Spring Harbor Laboratory Press, Cold Spring Harbor, N.Y.; Miller et al. (1987) *Gene Transfer Vectors for Mammalian Cells,* Cold Spring Harbor Laboratory Press, Cold Spring Harbor, N.Y.; Jakoby & Pastan (1979) *Meth. Enzymol.* 58, *Cell Culture;* and Joyner (1993) *Gene Targeting, A Practical Approach,* Oxford University Press, Oxford.

I. RVP, Packaging Cell Lines and Producer Cell Lines

The present invention relates to the discovery that certain non-primate mammalian cell lines are useful for producing high titers of human serum-resistant RVP. It was surprisingly found that, in contrast to previous studies, the presence or absence of the αGal moiety did not play a role in determining whether the RVP or cell lines were resistant to human serum. Further the chromosomal DNA of thse cell lines contain few, if any, endogenous retrovirus nucleic acid sequences. Accordingly, production of RVP in these cell lines is both easier and safer for gene therapy uses. RVP produced from the cell lines of the invention are not subject to lysis in the presence of human body fluids and, moreover, exhibit substantially no contamination by recombinantly-generated retroviruses.

The cell lines of the invention for preparation of packaging cell lines and producer cell lines include the αGal-positive ferret brain cell line Mpf, publically available from the American Type Culture Collection (ATCC) 12301 Parklawn Drive, Rockville, Md. 20852 USA as accession number ATCC 1656-CRL. Other cell lines included in the invention are those which have the properties of Mpf cells necessary for the practice of this invention, i.e., non-primate, αGal-positive, production of human serum-resistant RVP at high titer and lack of endogenous retroviral sequences. These cell lines can be from ferret brain or other non-primate source. In addition, the ovine MDOK cell line may be useful in the invention although it does not grow as well as Mpf cells. The preferred cell line is the Mpf cell line.

To determine whether a cell line lacks endogenous retroviral sequences, i.e., has substantially no endogenous retroviral sequences, the chromosomal DNA can be prepared from the cell line and subjected to hybridization under stringent washing conditions with a retrovirus probe of sufficient length to exhibit specific binding to any endogenous sequences that may be present. It is not necessary to screen the chromosomal DNA with many retrovirus probes, and in fact, any cell line that exhibits substantially no hybridization to a Moloney-MLV retrovirus probe under stringent washing conditions comes within the scope of the invention.

As used herein, "retroviral vector particles" or RVP are membrane-enveloped particles that are replication-defective retroviruses and contain a retrovirus vector capable of expressing a heterologous or foreign gene encoded thereon. The particles are capable of genetically modifying mammalian cells. The RVP of the invention are prepared from a producer cell line of the invention, e.g., from an Mpf producer cell line.

The terms "packaging cells" and "packaging cell lines" are used interchangeably herein. Packaging cell lines are cells that express a cellular targeting protein (e.g. retroviral env proteins) and gag/pol genes of retroviruses in a manner that permits packaging of retrovirus vectors into RVP. While retroviral tropism, or host range, is determined by the env protein, the use of any protein that has specificity for a target cell is contemplated since this allows the broadest possible host range for the RVP. Cellular targeting protein of the invention are proteins capable of targeting an RVP for delivery/binding to a human cell, whether those cells are dividing or non-dividing cells, in a manner that permits the retrovirus vector of the RVP to enter the target cell. The nature of the cellular targeting protein will determine the specificity of RVP in transducing target cells. Examples of cellular targeting proteins useful in the invention include retroviral amphotropic, xenotropic and polytropic retroviral env proteins, the JSRV env protein, vesicular stomatitis virus G protein and transferrin. In addition, gag proteins engineered to contain a nuclear localization signal can also be used in packaging vectors in accordance with the invention, especially when the gene therapy target cells are non-dividing. An example of one such gag protein is that obtained from the sheep retrovirus JSRV, a retrovirus that infects adult lung tissue (i.e., non-dividing cells) and leads to lung cancer.

General discussions of packaging cells and gene transfer using RVP can be found in various publications including PCT Patent Publication No. WO92/07943, EPO Patent Publication No. 178,220, U.S. Pat. No. 4,405,712, Gilboa (1986) Biotechniques 4:504–512; Mann et al. (1983) Cell 33:153–159; Cone and Mulligan (1984) Proc. Natl. Acad. Sci. USA 81:6349–6353; Eglitis et al. (1988) Biotechniques 6:608–614; Miller and Rosman (1989) Biotechniques 7:981–990; Morgenstern and Land (1990) Nucleic Acids Res 18:3587–3596; Eglitis (1991) Human Gene Therapy 2:195–201; Miller (1992); Mulligan (1993); and Ausubel et al. (1992) Current Protocols in Molecular Biology, Wiley Interscience, John Wiley and Sons, New York.

The packaging cells of the invention are produced by introducing one or more packaging vectors into the non-primate mammalian cultured cells of the invention (preferably Mpf cells); and recovering the desired packaging cells by selecting those cells of the culture which stably express the proteins encoded by the one or more packaging vectors. The packaging vectors are expression vectors comprising recombinant nucleic acid molecules encoding the retroviral pol and gag proteins and a cellular targeting protein. The packaging vectors can be introduced by transfection or other suitable techniques.

The manipulation of retroviral nucleic acids to construct packaging vectors and packaging cells is accomplished using techniques known in the art. See Ausubel et al. (1992) Volume 1, Section III (units 9.RVP.1–9.14.3); Sambrook et al. (1989); Miller and Rosman (1989); Eglitis et al. (1988); U.S. Pat. Nos. 4,650,764, 4,861,719, 4,980,289, 5,122,767, and 5,124,263; as well as PCT Patent Publications Nos. WO85/05629, WO89/07150, WO90/02797, WO90/02806, WO90/13641, WO92/05266, WO92/07943, WO92/14829, and WO93/14188. The packaging vectors described in WO89/07150 are particularly useful.

These manipulations typically involve the use of DNA copies of the gag, pol, and env retroviral genes cloned in plasmid vectors. Such plasmid vectors containing retroviral genes can be prepared by, for example, isolation of DNA copies of the viral genome from the cytoplasm of infected cells (using, for example, the method of Hirt (1967) J. Mol. Biol. 26:365–369), restriction digestion of the DNA copies of the viral genome (or PCR amplification of regions of interest of the DNA, generally followed by restriction digestion of the PCR product) to produce desired fragments, and multiple rounds of subcloning of the fragments, along with fragments containing suitable selectable marker and origin of replication sequences, to produce operable packaging vectors.

Multiple rounds of subcloning are used because it has been found that the typical bacterial cells used as plasmid hosts in subcloning, e.g., *E. coli,* tend to create deletions in the nucleotide sequences of newly inserted retroviral fragments when such fragments comprise more than about 4 kbp. Accordingly, construction of the final packaging vector proceeds more efficiently if small retroviral insert fragments (on the order of less than about 4 kbp) are sequentially assembled in the plasmid through multiple rounds of subcloning.

Once a packaging cell line has been established, the next step is to generate "producer cells" or "producer cell lines" by introducing retroviral vectors into the packaging cells and recovering the producer cell line, for example, by selecting for the presence of the retroviral vector. Examples of retroviral vectors are found in, for example, Korman et al. (1987) Proc. Natl. Acad. Sci. USA, 84:2150–2154; Miller and Rosman (1989); Morgenstern and Land, 1990; U.S. Pat. Nos. 4,405,712, 4,980,289, and 5,112,767; and PCT Patent Publications Nos. WO85/05629, WO90/02797, and WO92/07943. The retroviral vector includes a psi site and one or more heterologous nucleic acid sequences selected to perform a desired function, e.g., an experimental, diagnostic, or therapeutic function. These heterologous nucleic acid sequences are flanked by LTR sequences which function to direct high efficiency integration of the sequences into the genome of the ultimate target cell. The term "heterologous" gene or coding sequence is interchangeable with "foreign" gene or coding sequence.

Once a producer cell line is established, the cells are grown in culture under standard conditions to produce RVP. The RVP are released into the supernatant and can be harvested, purified and concentrated as needed using techniques know in the art. The preferred producer cell lines of the invention are derived from the Mpf cell line.

II. Gene Transfer for Gene Therapy

The many applications of gene therapy are well known and have been extensively reviewed [see, for example, Boggs (1990) Int. J. Cell Cloning 8:80–96; Kohn et al. (1989) Cancer Invest. 7:179–192; Lehn (1990) Bone Marrow Transplant. 5:287–293; Verma (1990) Sci. Am. 263:68–84; Weatherall (1991) Nature 349:275–276; and Felgner and Rhodes (1991) Nature 349:351–352].

A variety of genes and nucleic acid fragments encoding thereapeutic molecules or agents can be incorporated into the RVP of the invention for use in gene therapy. These nucleic acid fragments and genes may direct the expression of RNA and/or protein molecules that render them useful as therapeutic agents. Protein-encoding genes of use in gene therapy include those encoding various hormones, growth factors, enzymes, lymphokines, cytokines, receptors, angiogenic factors, anti-angiogenesis factors and the like.

Among the genes that can be transferred in accordance with the invention are those encoding polypeptides that are absent, are produced in diminished quantities, or are produced in mutant form in individuals suffering from a genetic disease. Other genes of interest are those that encode proteins that, when expressed by a cell, can adapt the cell to grow under conditions where the unmodified cell would be unable to survive, or would become infected by a pathogen. Genes that target transduced cells for destruction are useful for the treatment of neoplasias. Genes encoding proteins that have been engineered to circumvent a metabolic defect are also suitable for transfer into the cells of a patient using the methods and compositions of the present invention.

In addition to protein-encoding genes, the present invention can be used to introduce nucleic acid sequences directing the expression of medically-useful RNA molecules into cells. Examples of such RNA molecules include anti-sense molecules and catalytic molecules, such as ribozymes.

III. Preparation and Administration of RVP of the Invention

The present invention provides human serum resistant RVP with improved safety for administration to the body fluids of a patient. Significantly, the present invention allows for the use of more practical protocols for RVP administration. It does so by eliminating the need to remove the target cells from body fluids prior to administration of the RVP. Specifically, in accordance with the invention, the RVP are administered to cells while those cells are in contact with body fluids such as blood, plasma, serum, lymph, the fluids making up bone marrow, and the like. In addition the RVP can be administered in vivo, directly to the patient.

In general, to form packaging cells in accordance with the invention, the packaging vector or vectors described above are introduced into a non-primate mammalian cell line of the invention such as Mpf, and preferably into the Mpf cell line. The producer cells of the invention are prepared by the introduction of a retroviral vector into the packaging cells of the invention.

The producer cells of the invention are used to produce RVP by culturing the cells in a suitable growth medium. If desired, the particles can be harvested from the culture and administered to the target cells which are to be transduced, or the producer cells can be grown together with the target cells. The growth of producer cells together with target cells can be accomplished by co-culture of the cells in vitro, or, when desired, the producer cells are co-cultured together with the target cells by implantation of the producer cells in the patient.

In another embodiment which expedites rapid transduction by eliminating the need to wait for target cells to divide, and allows transduction of cells that divide slowly or not at all, a retroviral transduction system producing RVP that can transduce non-dividing cells may be preferred. Such transduction systems are disclosed in U.S. Pat. Nos. 5,576,201 and 5,580,766 and can be adapted for use with in present invention.

In particular, gene therapy can be carried out by a procedure in which a retroviral producer cell of the invention (i.e., cells engineered to produce RVP) is implanted into the body of the patient to be treated. This may be a particularly desirable procedure in the treatment of certain cancers. In vivo studies have demonstrated that procedures involving the implantation of producer cells into rat solid tumors can effectively deliver RVP to adjacent cells [Culver et al. (1992) Science 256:1550–1552]. In one variation of such procedures, producer cells are engineered to express the herpes simplex virus thymidine kinase (HSVTK) gene. Treatment of a patient with ganciclovir post-implantation kills the HSVTK-expressing producer cells as well as any immediately surrounding cells, which, in such procedures, are tumor cells. Thus the present invention can be adapted for delivery of HSVTK in gene therapy for use in conjunction with ganciclovir treatment.

In related studies, producer cells injected into the brain of rats or monkeys were shown to survive for approximately 15 days without proliferating [Ram et al. (1993) J. Neurosurg. 79:400–407]. The survival of xenogeneic producer cells in the primate brain is not surprising considering that the brain is an immunoprivileged site relative to complement activity [Widner and Brundin (1988) Brain Res. Rev. 13:287–324] and therefore, hyperacute rejection (HAR) commonly associated with xenotransplants into primates is less likely to occur in the brain. HAR of xenografts in primates normally occurs within minutes of transplantation due to the activation of the classical complement pathway by preexisting antibodies to alpha-galactosyl epitopes found on the surface of mammalian cells excluding man, apes and Old World monkeys [Galili et al. (1987) Proc. Natl. Acad. Sci. USA 84:1369–1373; and Neethling et al. (1994) Transplant. 57:959–963].

Accordingly, when implantation is performed, the producer cells are derived from Mpf cells since these are resistant to lysis by human serum. Implantation into the human brain is contemplated.

The RVP of the invention can be used for ex vivo gene therapy in accordance with various techniques known in the art. In general terms, these techniques involve the removal of target cells of interest from a patient, incubation of the target cells with the RVP of the invention, and reintroduction of the transduced target cells into the patient. Various procedures can be applied to the target cells while they are in the ex vivo state, including selection of subsets of the target cells prior to transduction, isolation of transduced cells, selection of subsets of isolated, transduced cells, propagation of target cells either before or after transduction, in cases where the cells are capable of proliferation, and the like.

Delivery of nucleic acid molecules of interest may also be accomplished ex viva or in vivo by administration of the RVP of the invention to a patient. In particular, in accordance with the invention, the RVP can be administered to the target cells while the cells are bathed in body fluids. Cells that have been removed from the body but kept in diluted or undiluted fluids of their natural milieu, are referred to herein as in the "ex vivo unwashed state". Specifically, the RVP may be administered to the target cells via administration to the body fluids bathing cells in the ex vivo unwashed state using otherwise conventional protocols for ex vivo transduction of target cells, or may be administered to body fluids in vivo through known delivery routes. In one such in vivo application, the injection of RVP directly into solid tissues is considered to be administration to body fluids, as the cells in solid tissues are bathed in interstitial fluids, and the RVP enter the target cells following mixture with such fluids. Solid tissues include skin, organs, muscles, tumors and the like.

Hence, the administration of the RVP can be performed locally, e.g., by aerosol, transmucosal, or transdermal delivery, or, more typically, by a systemic route, e.g., orally, intravenously, intraperitoneally, intramuscularly, transdermally, intradermally, subdermally, transmucosally, or intrathecally.

IV. Pharmaceutical Compositions

The RVP of the invention can be formulated as pharmaceutical compositions. Such compositions will generally include a pharmaceutically effective carrier, such as saline, buffered (e.g., phosphate buffered) saline, Hank's balanced salts solution (HBSS), Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. See, for example, Remington's Pharmaceutical Sciences, Mack Publishing Company, Philadelphia, Pa., 17th ed., 1985. The pharmaceutical compositions are suitable for use in a variety of drug delivery systems. Langer (1990) Science, 249:1527–1533, reviews various drug delivery methods currently in use. In some cases, the drug delivery system will be designed to optimize the biodistribution and/or pharmacokinetics of the delivery of the retroviral vector particles. See, for example, Remington's Pharmaceutical Sciences, supra, Chapters 37–39. For example, the particles can be incorporated in vesicles composed of substances such as proteins, lipids (for example, liposomes), carbohydrates, or synthetic polymers. See, for example, Langer, 1990, supra.

The pharmaceutical compositions of the invention can be administered in a variety of unit dosage forms. The dose will vary according to, e.g., the particular RVP or producer cell, the manner of administration, the particular disease being treated and its severity, the overall health and condition and age of the patient, and the judgment of the prescribing physician. Dosage levels for human subjects are generally between about $10^6$ and about $10^{11}$ colony forming units of RVP per patient per treatment. Producer cells are administered in sufficient numbers to produce therapeutic levels of RVP, e.g., at least about $10^3$–$10^4$ producer cells.

In terms of clinical practice, the compositions and methods of the present invention will have broad therapeutic utility in facilitating the treatment of a wide range of inherited and acquired diseases and medical conditions including, without limitation, hematologic diseases, cardiopulmonary diseases, endocrinological diseases, immunological diseases, neoplasias, and the like.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed in an exemplary embodiment may be made by one skilled in the art and it is intended that such modifications, changes, and substitutions are to be included within the scope of the present invention.

EXAMPLE 1

Materials and Methods

Cell survival of various cell lines was assessed using the Cell Growth Determination Kit, MTT Based, Catalog # CGD-1 from SIGMA Biosciences. The kit was used according to manufacturer's instructions as follows. Cells were plated at 15,000 cells/well in 96-well flat bottom microtiter plates, cultured overnight at 37° C. In the morning, the cells were washed twice in HBSS. Fifty microliters of serum dilutions in HBSS were added and the mixture was incubated at 37° C. for 30 minutes. The serum was removed by aspiration and the remaining cells were washed twice with HBSS before adding 100 μL of 90% D10 culture media/10% MTT solution and proceeding according to manufacturer's instructions.

Released reverse transcriptase was assayed according to the method described in Hoshino et al. (1984) Nature 310:324–325.

The biological assay for serum resistance was conducted by incubating 100 μL of RVP supernatant with 100 μL of pooled human serum (fresh or heat inactivated) at 37° C. for 30 to 40 minutes. The incubated mixtures were then plated onto indicator cell lines (either NIH3T3 cells or Mv-1-Lu cells) in the presence of 8 μg/mL of polybrene at 37° C. overnight. Colony forming units were assessed in selective G418-containing media as described by Rother et al. (1995) Hum. Gene Ther. 6:429–435.

Flourescence-activated cell sorting (FACS) analysis for the presence of the αGal moiety was conducted as described in Kadan (1992) J. Virol. 66:2281–2287.

Immunogold staining was generally done in accordance with the methods described in Stirling (1990) J. Histochem. Cytochem. 38:145–157.

EXAMPLE 2

Analysis of Cell Lines

Seventeen cell lines from nine different species were analyzed for resistance to killing by human serum. The species and cell lines were as follows: human (HT1080, MRC-5, HeLa, WISH), mouse (NIH3T3), hamster (Hak, Dede, CHL, CHO-DHFR, AHL, BHK), fox (FoLu), ferret (Mpf), sheep (MDOK), opossum (OK), gerbil (GeLu) and guinea pig (JH4).

Human sera were collected from multiple healthy donors, pooled and incubated with cells undiluted (100% sera) or diluted in HBSS to 75, 50 and 25% sera with cell survival assessed as described in Example 1. The cells fell into three categories: fully resistant, partially resistant or very sensitive (FIG. 1).

The NIH3T3, JHK, OK and FoLu cells were very sensitive to killing by human serum. (Note: the OK cells gave identical data points as NIH3T3 cells and its symbol is obscured by that of NIH3T3 cells.) The NIH3T3 cells were selected to serve as a serum-sensitive control cell line. The partially resistant cell lines include GeLu, CHO-DHFR, Dede, CHL, AHL, Hak and BHK. All the human cell lines (HeLa, HT1080, MRC-5 and WISH) were completely resistant to killing by human serum and the HT1080 was selected to serve as a serum-resistant control. Two non-primate cell lines were fully resistant to killing by human serum, Mpf and MDOK, and evaluated further for production of human serum resistant RVP.

EXAMPLE 3

Generation of Producer Cell Lines and RVP

The HT1080, Mpf, Mv-1-Lu (mink lung fibroblasts) and NIH3T3 cell lines were used for generation of helper-contaminated producer cell lines bearing different retroviral env proteins with tropism for human cells. The four cell lines were transduced with the amphotropically-packaged retroviral vector LNCX [Miller and Rosman (1989)] and selected in G418 to generate populations of fully selected cells bearing this retroviral vector. MDOK cells grew poorly under these conditions and were not used further. The LNCX-transduced populations of cells were then infected with one of three replication competent retroviruses—4070A amphotropic, $NZB_{9-1}$ xenotropic, and MCF 13–81 polytropic—to generate helper-contaminated producer cell lines of the LNCX vector. Table 1 indicates that all the cell lines produce appreciable amounts of RVP with the exception of HT1080 cells which do not support productive infection by MCF 13–81 and NIH3T3 cells which do not support xenotropic virus propagation. Supernatents from these cell lines were exposed to equal volumes of human serum with active complement (fresh serum), human serum with complement inactivated by heat treatment (heated serum), or D10 media alone followed by assay of released reverse transcriptase as an indicator of virolysis. This assay can not distinguish between RVP and replication competent retroviruses generated during RVP production.

Virolytic capacity of serum differs between individuals as well as in the same individuals collected at different times. Serum also loses its virolytic capacity upon storage for a few months at −80° C. or in liquid nitrogen. To compensate for the variability in virolytic capacity in serum pools, the reverse transcriptase activity from fresh serum was compared to that released by heated human serum. A ratio of 1.0 indicates the ideal situation where there is no effect of active human serum on RVP virolysis. Since none of the ratios reached 1.0, there is always some negligible, but measurable, background level of virolysis contributed by fresh serum. Notably, however, the Mpf cell line generated RVP having the lowest ratios and therefore the most serum resistant RVP of this study for all types of viruses. HT1080 generated the next most serum resistant RVP for the xenotropic and amphotropic viruses. The MCF virus could not be tested on this cell line. The Mv-1-Lu cells generate RVP of equal serum resistance to HT1080 for amphotropic virus but not for MCF or xenotropic virus. NIH3T3 cells, as expected, generate RVP that are very sensitive to virolysis using amphotropic and MCF virus. (Xenotropic virus do not productively infect NIH3T3 cells.) The GPL cell line is an NIH3T3 based cell line which expresses gag-pol from plasmid gaq-pol-gpt, has been transduced multiple times with the LNL6 vector [Miller and Rosman (1989)] and fully selected in G418 to generate an "envelope tester' cell line which produces RVP containing no retroviral env protein. The RVP from the GPL cell line were also lysed by human serum, indicating that the presence of retroviral env proteins in RVP is not necessary for virolysis.

In addition to the biochemical reverse trancriptase assay, RVP were demonstrated to be human serum resistant in a biological assay. In this assay, supernatents of helper-contaminated RVP bearing the LNCX vector were exposed to heat-inactivated FBS (HI-FBS), heat-inactivated human serum pools (HI-HS) and fresh human serum pools (HS) and then titered for neomycin resistance on NIH3T3 and Mv-1-Lu cells as described in Example 1. Unlike the reverse transcriptase assay, this assay does not detect replication competent retroviruses because only RVP bearing the LNCX vector are scored in the assay.

Aliquots of helper-contaminated RVP were incubated in the presence of 90% pooled sera and titered on NIH3T3 cells for the amphotropic and MCF viruses, and on Mv-1-Lu cells for the xenotropic virus (FIG. 2A). The results show that for all three viruses tested, RVP from Mpf cells are serum resistant at levels equal to or greater than those for RVP from HT1080 cells. Conversely, amphotropic and MCF RVP generated from NIH3T3 cells are exceedingly sensitive to fresh human serum. Comparing the virolysis for HI-FBS and HI-HS demonstrate that there is no specific component of HI-HS which has virolytic properties or otherwise lowers the biological titer of RVP. However, in agreement with the reverse transcriptase results, fresh human serum produces negligibly, but consistently, lower RVP titer than those obtained in the presence of HI-HS. Again, this suggests that there is a low level of virolysis in the presence of fresh serum. This basal level of virolysis is inconsequential compared to the number of RVP that escape virolysis.

On Mv-1-Lu cells, the xenotropic samples had higher titers than the others in this assay. Therefore, the biological assay was repeated using Mv-1-Lu cells as the titer assay line for all samples (FIG. 2B). The results confirmed the findings of FIG. 2A. The data in FIGS. 2A and 2B represent titers of virus present in the assay, whereas the actual supernatents have titers about 100-fold higher. Hence, the Mpf titers for the xenotropic and MCF viruses are in the upper range of $10^6$ neo cfu/mL.

TABLE 1

| | | | CPM | | | |
|---|---|---|---|---|---|---|
| Cell line | RCR Virus | Media Bkgd | Total lysis | Fresh Serum | Heated Serum | Fresh/Heated Ratio |
| HT1080 | Ampho | 100 ± 4 | 6402 ± 250 | 653 ± 41 | 225 ± 13 | 2.9 |
| Mpf | | 131 ± 11 | 2365 ± 102 | 359 ± 18 | 153 ± 6 | 2.3 |
| Mv-1-Lu | | 54 ± 4 | 4511 ± 192 | 722 ± 11 | 253 ± 11 | 2.9 |
| NIH 3T3 | | 78 ± 7 | 11925 ± 334 | 5158 ± 269 | 160 ± 12 | 32.2 |
| HT1080 | MCF | 78 ± 4 | (8) ± 3 | 29 ± 6 | 15 ± 6 | ND |
| Mpf | | 192 ± 6 | 11876 ± 586 | 1514 ± 50 | 885 ± 43 | 1.7 |
| Mv-1-Lu | | 131 ± 7 | 6973 ± 393 | 1093 ± 31 | 135 ± 8 | 8.1 |
| NIH 3T3 | | 60 ± 6 | 12388 ± 217 | 3258 ± 123 | 223 ± 3 | 14.6 |
| HT1080 | Xeno | 68 ± 0 | 3051 ± 106 | 92 ± 8 | 50 ± 4 | 1.8 |
| Mfp | | 234 ± 22 | 3790 ± 33 | 421 ± 34 | 273 ± 14 | 1.5 |
| Mv-1-Lu | | 110 ± 6 | 998 ± 66 | 131 ± 12 | 35 ± 12 | 3.7 |
| GPL | None | 98 ± 4 | 778 ± 14 | 625 ± 32 | 58 ± 5 | 10.7 |

All values are from experiment done in triplicate and have standard errors of the mean of 10% or less. All assays were done at least three times giving similar results. Background CPM of media has been subtracted out from other values shown.
ND indicates not determined due to the fact that the MCF 13-81 virus does not productively infect HT1080 cells.

EXAMPLE 4

Determination of Endogenous Retroviral Sequences

The three cell types, NIH3T3, HT1080 and Mpf, were evaluated by Southern blotting for the presence of endogenous retroviral sequences, particularly for homology to gag-pol and env sequences. In this experiment, 10 μg of EcoRI-digested chromosomal DNA from each cell line was probed with a Moloney-MLV gag-pol specific probe and washed under stringent conditions. Only the NIH3T3 cells showed significant amounts of endogenous sequences by hybridizing to the gag-pol probe. The Mpf and HT1080 cells had no significant endogenous sequences hybridizing to the gag-pol probe. A second blot was probed with an amphotropic envelope probe and also washed under stringent conditions. Again, the Mpf cells showed no significant levels of hybridization to endogenous envelope sequences, whereas the HT1080 cells showed considerable amounts of endogenous envelope sequences hybridizing to the envelope probe. The NIH3T3 cells showed little or no endogenous envelope sequences hybridizing to the envelope probe.

EXAMPLE 5

FACS Analysis for the αGal Moiety

To examine the role of the αGal moiety in serum resistance of cell lines, flow cytometry on each of the seventeen cell lines described in Example 2 was performed using a fluorescently-conjugated, lectin-specific to the αGal moiety. The presence of αGal was compared to the serum resistance levels of the cell lines and is shown in Table 2. The cell lines ranged from strongly αGal positive to αGal negative without any apparent pattern correlatable to species with the exception that the human cells were all αGal negative.

TABLE 2

| | α Gal | |
|---|---|---|
| Serum sensitivity | Positive | Negative |
| Resistant | MDOK | HeLa |
| | Mpf | HT1080 |
| | | MRC-5 |
| | | WISH |

TABLE 2-continued

| | α Gal | |
|---|---|---|
| Serum sensitivity | Positive | Negative |
| Partial | AHL | BHK |
| | CHL | CHO-DHFR |
| | Hak | Dede |
| | | GeLu |
| Sensitive | FoLu | JH4 |
| | NJH 3T3 | |
| | OK | |

EXAMPLE 6

Immunogold Electron Microscopy of RVP

While Example 5 demonstrated that the human serum sensitivity of the cell lines did not correlate with the presence of the αGal moiety, it did not assess whether there was a correlation of human serum sensitivity with the presence of the αGal moiety on RVP generated from these cell lines.

Amphotropic, helper-contaminated RVP were collected from Mpf, HT1080 and NIH3T3 cells and defective, envelope protein-minus RVP were collected from GPL cells. Immunogold electron microscopy was performed on these RVP using gold-conjugated anti-αGal lectin. As expected, the amphotropic RVP prepared from HT1080 cells lacked gold particle binding, whereas the RVP from the NIH3T3 cell were decorated with large amounts of bound gold particles. Consistent with the FACS results for Mpf cells, the RVP prepared from Mpf cells showed an intermediate amount of gold particle binding, indicating that Mpf-derived RVP are αGal positive. In addition, RVP prepared from GPL cells, which are smaller in size due to the lack of envelope proteins, were strongly αGal positive, demonstrating that the αGal moiety is not merely present on retroviral envelope proteins.

I claim:

1. A method for preparing a stable, retroviral packaging cell line for generation of human serum-resistant retroviral vector particles (RVP) which comprises:
   (a) introducing one or more packaging vectors into a fully human serum-resistant non-primate mammalian cell line, wherein said cell line exhibits no specific hybridization to a Moloney-MLV retrovirus gag-pol or env probe and is capable of producing fully human-serum-resistant RVP and wherein said vectors, either singly or collectively, express a cellular targeting protein and retroviral gag and pol genes in amounts sufficient to package said RVP; and (b) recovering said packaging cell line.

2. The method of claim 1, wherein said cellular targeting protein is an amphotropic retroviral env protein, a xenotropic retroviral env protein, a polytropic retroviral env protein, a JSRV env protein, vesicular stomatitis virus G protein or transferrin.

3. A packaging cell line produced by the method of claim 1 or 2.

4. A method for preparing a stable, retroviral producer cell capable of producing human serum-resistant retroviral vector particles (RVP) which comprises (a) introducing a retrovirus vector into the packaging cell line of claim 1, wherein said retrovirus vector is capable of being packaged into an RVP and comprises a heterologous gene capable of expression in a human; and (b) recovering said producer cells.

5. A method for preparing human serum-resistant retroviral vector particles (RVP) which comprises:

(a) introducing a retrovirus vector into the packaging cell line of claim 1, wherein said retrovirus vector is capable of being packaged into an RVP and comprises a heterologous gene capable of expression in a human;

(b) culturing said cell line for a time and under conditions sufficient to produce said RVP; and (c) recovering said RVP.

6. The method of claim 4, wherein said cells are α-galactosyl positive.

7. The method of claim 4, wherein said cellular targeting protein is an amphotropic retroviral env protein, a xenotropic retroviral env protein, a polytropic retroviral env protein, a JSRV env protein, vesicular stomatitis virus G protein or transferrin.

8. Producer cells prepared by the method of claim 4.

9. A method for preparing human serum-resistant retroviral vector particles (RVP) which comprises:

(a) culturing the producer cells of claim 4 for a time and under conditions sufficient to produce said RVP; and (c) recovering said RVP.

10. The method of claim 5, wherein said cell line is α-galactosyl positive.

11. The method of claim 5, wherein said cellular targeting protein is an amphotropic retroviral env protein, a xenotropic retroviral env protein, a polytropic retroviral env protein, a JSRV env protein, vesicular stomatitis virus G protein or transferrin.

12. The method of claim 9, wherein said cells are α-galactosyl positive.

13. The method of claim 9, wherein said cellular targeting protein is an amphotropic retroviral env protein, a xenotropic retroviral env protein, a polytropic retroviral env protein, a JSRV env protein, vesicular stomatitis virus G protein or transferrin.

14. A method for preparing a stable, retroviral packaging cell line for generation of human serum-resistant retroviral particles (RVP) which comprises (a) introducing one or more packaging vectors into a non-primate mammalian cell that is human serum resistant in 100% human serum, wherein said vectors, either singly or collectively, express a cellular targeting protein and retroviral gag and pol genes in amounts sufficient to package said RVP; and (b) recovering said packaging cell line.

15. The method of claim 14, wherein said cell line exhibits no specific hybridization to a Moloney-MLV retrovirus gag-pol or env probe.

16. The method of claim 14, wherein said cellular targeting protein is an amphotropic retroviral env protein, a xenotropic retroviral env protein, a polytropic retroviral env protein, a JSRV env protein, vesicular stomatitis virus G protein or transferrin.

17. A packaging cell line produced by the method of claim 14.

18. A method for preparing stable, retroviral producer cells capable of producing human serum-resistant retroviral vector particles (RVP) which comprises (a) introducing a retrovirus vector into the packaging cell line of claim 14, wherein said retrovirus vector is capable of being packaged into an RVP and comprises a heterologous gene capable or expression in a human; and (b) recovering said producer cells.

19. A method for preparing human serum-resistant retroviral vector particles (RVP) which comprises:

(a) introducing a retrovirus vector into the packaging cell line of claim 14, wherein said retrovirus vector is capable of being packaged into an RVP and comprises a heterologous gene capable of expression in a human;

(b) culturing said cell line for a time and under conditions sufficient to produce said RVP; and (c) recovering said RVP.

20. The method of claim 18, wherein said cells exhibit no specific hybridization to a Moloney-MLV retrovirus gag-pol or env probe.

21. The method of claim 18, wherein said cellular targeting protein is an amphotropic retroviral env protein, a xenotropic retroviral env protein, a polytropic retroviral env protein, a JSRV env protein, vesicular stomatitis virus G protein or transferrin.

22. Producer cells prepared by the method of claim 18.

23. The method of claim 19, wherein said cell line exhibits no specific hybridization to a Moloney-MLV retrovirus gag-pol or env probe.

24. The method of claim 19, wherein said cellular targeting protein is an amphotropic retroviral env protein, a xenotropic retroviral env protein, a polytropic retroviral env protein, a JSRV env protein, vesicular stomatitis virus G protein or transferrin.

25. A method for preparing human serum-resistant retroviral vector particles (RVP) which comprises:

(a) culturing the producer cells of claim 18 for a time and under conditions sufficient to produce said RVP; and (b) recovering said RVP.

26. The method of claim 25, wherein said cells exhibit no specific hybridization to a Moloney-MLV retrovirus gag-pol or env probe.

27. The method of claim 25, wherein said cellular targeting protein is an amphotropic retroviral env protein, a xenotropic retroviral env protein, a polytropic retroviral env protein, a JSRV env protein, vesicular stomatitis virus G protein or transferrin.

* * * * *